(12) United States Patent
Anderson et al.

(10) Patent No.: US 10,145,815 B2
(45) Date of Patent: Dec. 4, 2018

(54) PHOTOSWITCHABLE GRAPHENE MEMBRANES

(71) Applicant: EMPIRE TECHNOLOGY DEVELOPMENT LLC, Wilmington, DE (US)

(72) Inventors: Kraig K. Anderson, San Mateo, CA (US); Angele Sjong, Louisville, CO (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 138 days.

(21) Appl. No.: 15/027,170

(22) PCT Filed: Oct. 7, 2013

(86) PCT No.: PCT/US2013/063732
§ 371 (c)(1),
(2) Date: Apr. 4, 2016

(87) PCT Pub. No.: WO2015/053744
PCT Pub. Date: Apr. 16, 2015

(65) Prior Publication Data
US 2016/0245772 A1    Aug. 25, 2016

(51) Int. Cl.
*G01N 27/30* (2006.01)
*B05D 3/06* (2006.01)
(Continued)

(52) U.S. Cl.
CPC ............ *G01N 27/305* (2013.01); *B05D 3/06* (2013.01); *B05D 3/065* (2013.01); *B05D 5/00* (2013.01);
(Continued)

(58) Field of Classification Search
CPC ..... C01B 32/182; C01B 32/198; B32B 27/00; B32B 27/02; C07C 245/06; C07C 245/08;
(Continued)

(56) References Cited

U.S. PATENT DOCUMENTS

| | | | |
|---|---|---|---|
| 8,221,592 | B2 | 7/2012 | Lee |
| 2007/0104922 | A1 | 5/2007 | Zhai et al. |

(Continued)

FOREIGN PATENT DOCUMENTS

| | | |
|---|---|---|
| CN | 1032877 | 5/1989 |
| EP | 0504419 A1 | 9/1992 |
| WO | 2012110745 A1 | 8/2012 |

OTHER PUBLICATIONS

"Self-assembled Graphene/Azo Polyelectrolyte Multilayer Film and Its Application in Electrochemical Energy Storage Device", Dongrui Wang et al. Langmuir, Issue 5, vol. 27, Jan. 18, 2011.

(Continued)

*Primary Examiner* — Kregg T Brooks

(57) ABSTRACT

Graphene composites are disclosed. The graphene composites may include, for example, a photoswitchable layer, a graphene layer, and a substrate. The graphene composites may, in some embodiments, include a graphene layer with photoswitchable surface characteristics. Methods of making the graphene composite are further disclosed. Devices and systems configured to make and use the composites are also disclosed.

21 Claims, 9 Drawing Sheets

100 - Graphene Composite
105 - Substrate
110 - Photoswitchable layer
115 - Graphene Layer

(51) Int. Cl.
| | |
|---|---|
| B05D 5/00 | (2006.01) |
| B05D 7/00 | (2006.01) |
| C01B 32/182 | (2017.01) |
| C07C 245/08 | (2006.01) |
| H01B 1/04 | (2006.01) |
| B82Y 30/00 | (2011.01) |

(52) U.S. Cl.
CPC .............. *B05D 7/54* (2013.01); *C01B 32/182* (2017.08); *C07C 245/08* (2013.01); *H01B 1/04* (2013.01); *B82Y 30/00* (2013.01)

(58) Field of Classification Search
CPC ........ B82Y 30/00; G01N 27/305; H01B 1/04; B05D 3/06; B05D 3/065
See application file for complete search history.

(56) References Cited

U.S. PATENT DOCUMENTS

| | | |
|---|---|---|
| 2007/0134420 A1 | 6/2007 | Koberstein et al. |
| 2012/0214172 A1 | 8/2012 | Chen et al. |
| 2013/0200302 A1 | 8/2013 | Miller |
| 2013/0216830 A1 | 8/2013 | Han et al. |

OTHER PUBLICATIONS

"Light-Driven Motion Liquids on a photoresponsive Surface", Kunihiro Ichimura et al. Science, Issue 5471, vol. 288, Jun. 2, 2000.
"Photoreversibly Switchable Superhydrophobic Surface with Erasable and Rewritable Pattern", Ho Sun Lim et al. Journal of American Chemical Society, Issue 45, vol. 128, Oct. 21, 2006.
"Phototunable Temperature-Responsive Molecular Brushes Prepared by ATRP", Hyung-il Lee et al. Macromolecules, Issue 11, vol. 39, May 6, 2006.
Office Action dated Mar. 31, 2017 from Chinese Application No. 2013800801041, including English Summary.
Cho, "Beyond Self-Cleaning: Switchable Surfaces," accessed at https://web.archive.org/web/20140808125848/http://www.scientificamerican.com/article/beyond-self-cleaning-switchable-surfaces/, Jul. 21, 2008, pp. 1-2.
Bao, W., et al., "Controlled ripple texturing of suspended graphene and ultrathin graphite membranes," Nature Nanotechnology, vol. 4, pp. 562-566 (Jul. 26, 2009).
Chen, M., and Besenbacher, F., "Light driven wettability changes on a photoresponsive electrospun mat," ACS Nano, vol. 5, Issue 2, pp. 1549-1555 (Feb. 2, 2011).
International Search Report and Written Opinion for International Application No. PCT/US2013/63732 dated Mar. 7, 2014.
Jiang, W.H., et al., "Photo-Switched Wettability on an Electrostatic Self-Assembly Azobenzene Monolayer," Chem. Commun., Issue 28, pp. 3550-3552 (Jun. 9, 2005).
Lee, H-I., et al., "Phototunable temperature-responsive molecular brushes prepared by ATRP," Macromolecules, vol. 39, Issue 11, pp. 3914-3920 (May 6, 2006).
Lim, H.S., et al., "Photoreversibly switchable superhydrophobic surface with erasable and rewritable pattern," Journal of the American Chemical Society, vol. 128, Issue 45, pp. 14458-14459 (Oct. 21, 2006).
Liu, L-H., et al., "A simple and scalable route to wafer-size patterned graphene," Journal of Material Chemistry, vol. 20, Issue 24, pp. 5041-5046 (May 17, 2010).
Margapoti, E., et al., "Direct observation of photo-switchable quasi-bound states in a Graphene-Azobenzene-Au multilayer," Condensed Matter, Materials Science, pp. 1-12 (Aug. 2, 2013).
Pei, X., et al., "Correlation between the Structure and Wettability of Photoswitchable Hydrophilic Azobenzene Monolayers on Silicon," Langmuir, vol. 27, No. 15, pp. 9403-9412 (Jun. 23, 2011).
Rabolt, J., et al., "Enhancing the properties of nanoscale electrospun polymer fibers through chemical architecture, surface texturing and optimization of processing protocols," NSF Nanoscale Science and Engineering Grantees Conference, pp. 3 (Dec. 16-18, 2003).
Rafiee, J., et al., "Wetting transparency of graphene," Nature Materials, vol. 11, pp. 1-6 (Jan. 22, 2012).
Yang, C., et al., "Influence of surface roughness on superhydrophobicity," Physical Review Letters, vol. 97, Issue 11, pp. 116103-1-116103-5 (Sep. 30, 2006).
Zhang, X., et al., "Enhanced Reversible Photoswitching of Azobenzene-Functionalized Graphene Oxide Hybrids," Langmuir, vol. 26, No. 23, pp. 18508-18511 (Nov. 8, 2010).
Zhang, X., et al., "Highly hydrophobic and adhesive performance of graphene films," Journal of Materials Chemistry, vol. 21, Issue 33, pp. 12251-12258 (Jul. 13, 2011).
Caldwell, J.D., et al., "Technique for the Dry Transfer of Epitaxial Graphene onto Arbitrary Substrate," American Chemical Society Nano, vol. 4, No. 2, pp. 1108-1114 (Jan. 25, 2010).
Li, X., et al., "Transfer of Large-Area Graphene Films for High-Performance Transparent Conductive Electrodes," Nano Letters, vol. 9, No. 12, pp. 4359-4363 (Oct. 21, 2009).

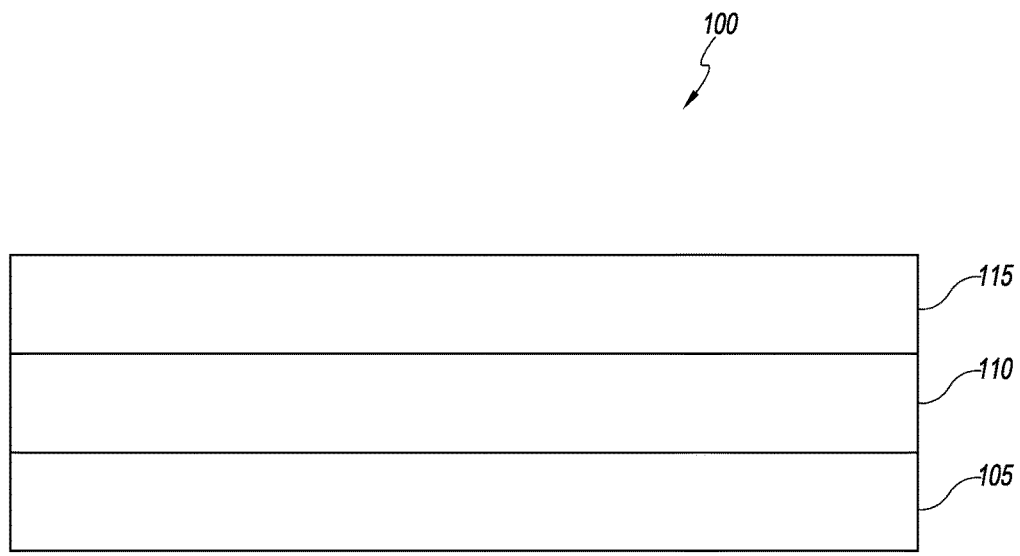
100 - Graphene Composite
105 - Substrate
110 - Photoswitchable layer
115 - Graphene Layer
FIG. IA

*120* - Azobenzene

US 10,145,815 B2

PHOTOSWITCHABLE GRAPHENE MEMBRANES

CROSS-REFERENCE TO RELATED APPLICATION

This Application is a U.S. National Stage filing under 35 U.S.C. § 371 of International Application No. PCT/US2013/063732 filed on Oct. 7, 2013. The International Application is herein incorporated by reference in its entirety.

BACKGROUND

Unless otherwise indicated herein, the materials described in this section are not prior art to the claims in this application and are not admitted to be prior art by inclusion in this section.

Wettability of a solid surface is a characteristic of materials used for varying applications, including membranes and sensors. Hydrophobic surfaces are typically insulating, and thus highly conductive surfaces, such as graphene, tend not to be hydrophobic and lack wettability.

SUMMARY

The foregoing summary is illustrative only and is not intended to be in any way limiting. In addition to the illustrative aspects, embodiments, and features described above, further aspects, embodiments, and features will become apparent by reference to the drawings and the following detailed description.

In some embodiments, provided is a graphene composite comprising: a photoswitchable layer configured to reversibly change between a hydrophobic state and a hydrophilic state; a graphene layer disposed on the photoswitchable layer; and a substrate, wherein the photoswitchable layer is disposed between the substrate and the graphene layer.

Also provided are methods of making a graphene composite comprising: providing a substrate; forming a photoswitchable layer on the substrate, the photoswitchable layer being configured to reversibly change between a hydrophobic state and a hydrophilic state; and applying graphene to the photoswitchable layer.

Some embodiments provide a method comprising: providing a graphene composite comprising: a photoswitchable layer configured to reversibly change between a hydrophobic state and a hydrophilic state; a graphene layer disposed on the photoswitchable layer; and a substrate, wherein the photoswitchable layer is disposed between the substrate and the graphene layer; applying a first radiation to the photoswitchable layer effective to cause at least a portion of the photoswitchable layer to be in the hydrophobic state; and applying a second radiation to the photoswitchable layer effective to cause at least a portion of the photoswitchable layer to be in the hydrophilic state.

Also provided are methods of sensing one or more analytes in a sample, the methods comprising: providing a graphene composite comprising: a photoswitchable layer configured to reversibly change between a hydrophobic state and a hydrophilic state; a graphene layer disposed on the photoswitchable layer; and a substrate, wherein the photoswitchable layer is disposed between the substrate and the graphene layer; applying a first radiation to the photoswitchable layer effective to cause at least a portion of the photoswitchable layer to be in the in the hydrophobic state; contacting the sample with the graphene layer while the photoswitchable layer is in the hydrophobic state; applying a first voltage to the graphene layer such that a first current flows in the graphene layer; and measuring the first current in the graphene layer while the first voltage is applied.

Some embodiments provide a device comprising: a graphene composite comprising: a photoswitchable layer configured to reversibly change between a hydrophobic state and a hydrophilic state; a graphene layer disposed on the photoswitchable layer; and a substrate, wherein the photoswitchable layer is disposed between the substrate and the graphene layer; a first light source configured to apply a first radiation to the photoswitchable layer effective to cause at least a portion of the photoswitchable layer to be in the hydrophobic state; and a second light source configured to apply a second radiation to the photoswitchable layer effective to cause at least a portion of the photoswitchable layer to be in the hydrophilic state.

Further provided are systems for making a graphene composite, the systems comprising: a controller; a photoswitchable layer applicator configured via the controller to apply a photoswitchable layer, or a precursor thereof, to a substrate; and a graphene applicator configured via the controller to apply graphene to the photoswitchable layer.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings.

FIGS. 1A-B show examples of a graphene composite in accordance with at least some embodiments of the present disclosure.

DETAILED DESCRIPTION

Figure 1B:
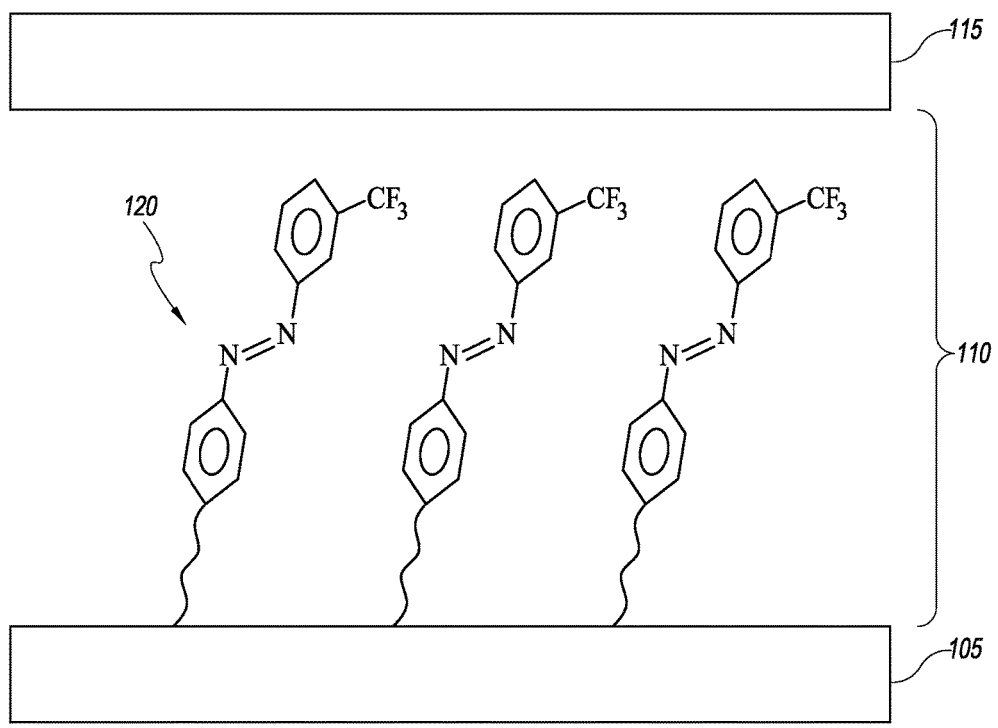

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented here. The aspects of the present disclosure, as generally described herein, and illustrated in the Figures, can be arranged, substituted, combined, and designed in a wide variety of different configurations, all of which are explicitly contemplated and made part of this disclosure.

Briefly stated, described herein are graphene composites. The graphene composites may include, for example, a photoswitchable layer, a graphene layer, and a substrate. The graphene composites may, in some embodiments, include a graphene layer with photoswitchable surface characteristics. Methods of making the graphene composite are further disclosed. Devices and systems configured to make and use the composites are also disclosed.

As used herein, "alkyl" refers to a straight or branched hydrocarbon chain that comprises a fully saturated (no double or triple bonds) hydrocarbon group. The alkyl group of the compounds may be designated as "$C_1$-$C_4$ alkyl" or similar designations. By way of example only, "$C_1$-$C_4$ alkyl" may indicate that there are one to four carbon atoms in the alkyl chain, e.g., the alkyl chain may be selected from methyl, ethyl, propyl, iso-propyl, n-butyl, iso-butyl, sec-butyl, and t-butyl. Typical alkyl groups may include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as defined above. A non-limiting list of alkoxys may include methoxy, ethoxy, n-propoxy, 1-methylethoxy (isopropoxy), n-butoxy, iso-butoxy, sec-butoxy, tert-butoxy, and the like.

As used herein, "haloalkyl" refers to an alkyl group in which one or more of the hydrogen atoms are replaced by a halogen (e.g., mono-haloalkyl, di-haloalkyl and tri-haloalkyl). Such groups may include but are not limited to, chloromethyl, fluoromethyl, difluoromethyl, trifluoromethyl, 1-chloro-2-fluoromethyl and 2-fluoroisobutyl.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups may include but are not limited to, chloromethoxy, fluoromethoxy, difluoromethoxy, trifluoromethoxy, 1-chloro-2-fluoromethoxy and 2-fluoroisobutoxy.

As used herein, the term "$C_{1-20}$-alkylene," either alone or in combination with another radical, refers to a divalent alkyl radical derived by removal of two hydrogen atoms from an aliphatic hydrocarbon containing one to twenty carbon atoms which may optionally be unsaturated, so as to contain one or more double or triple bonds, or may additionally optionally contain one or more heteroatoms (e.g., one, two, three, or more heteroatoms) each independently selected from N, O and S. Examples of alkylene groups may include, but are not limited to, —CH$_2$—, —CH$_2$CH$_2$—, —CH$_2$CH$_2$CH$_2$—, —CH$_2$CH(Me)-, —(CH$_2$)$_5$—CH—CH$_2$—, —(CH$_2$)$_3$—O—(CH$_2$)$_3$—(CH$_2$)$_2$—NH—(CH$_2$)$_4$—, and —(CH$_2$)$_3$—O—CH$_2$CH—CH$_2$—.

Some embodiments disclosed herein include a graphene composite having a photoswitchable layer, a graphene layer, and a substrate. The composition may, for example, exhibit photoswitchable wettability. FIG. 1A shows one example of graphene composite 100 in accordance with at least some embodiments of the composition in the present disclosure. Photoswitchable layer 110 may be disposed between graphene layer 115, and substrate 105. Photoswitchable layer 110 may be configured to reversibly change between a hydrophobic state and a hydrophilic state. Substrate 105 may, for example, include silicon or silica.

Graphene layer 115 may be disposed on the photoswitchable layer 110. Graphene layer 115 may be disposed within 5.0 nm, 4.0 nm, 3.0 nm, 2.5 nm, 2.0 nm, or 1.5 nm of the photoswitchable layer. Graphene layer 115 may be disposed directly on the photoswitchable layer 110.

Photoswitchable layer 110 may, for example, include a photoisomerization compound that can undergo a cis-trans isomerization when a specified wavelength of light is applied to the photoisomerization compound. The photoisomerization compounds can be configured so that the surface of the photoswitchable layer 110 can be hydrophobic in the trans configuration and hydrophilic in the cis configuration (or vice-versa). For example, numerous azobenzene compounds may be used to form photoswitchable layers that can have their surface properties modulated by applying light that induces a cis-trans isomerization. Generally, azobenzene compounds can exhibit hydrophobic surface properties in the trans isomer and hydrophilic surface properties in the cis isomer. Ichimura, K. et al., "Light-Driven Motion of Liquids on a Photoresponsive Surface," *Nature*, (2008), Vol. 288, pp. 1624-26 discloses macrocyclic compounds including an azobenzene unit that forms a photoswitchable monolayer on a silica substrate. Ultraviolet light and blue light may be applied to the photoswitchable layer to modify the surface properties. Other non-limiting examples of photoswitchable layers including an azobenzene compound are disclosed in: (i) Lim, H. et al., "Photoreversibly Switchable Superhydrophobic Surface with Erasable and Rewritable Pattern," *Journal of the American Chemical Society*, (2006), Vol. 128, pp. 14458-59; (ii) European Patent Publication No. EP0504419A1; and (iii) U.S. Pat. No. 8,221,592.

In some embodiments, the photoswitchable layer 110 may include at least one azobenzene compound. The azobenzene compound may be represented by formula (I):

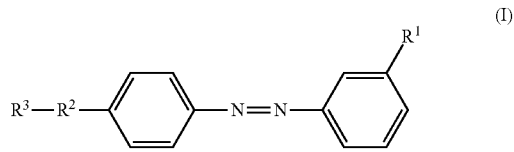

where $R^1$ is a hydrophobic moiety, $R^2$ is a spacer group, and $R^3$ is a coupling group. The hydrophobic moiety, in some embodiments, may be an alkyl, a haloalkyl, an alkoxy, a haloalkoxy, or a halogen. For example, hydrophobic moiety may be trifluoromethyl. In some embodiments, the spacer group may be a $C_{1-20}$-alkylene. In some embodiments, the coupling group may be an amine, a carboxylic acid, a thiol, or a silane coupling group. For example, the coupling group, prior to coupling, can be a trimethoxy silyl. The azobenzene compounds of formula (I) may be prepared using standard techniques. For example, "Photoreversibly Switchable Superhydrophobic Surface with Erasable and Rewritable Pattern," *Journal of the American Chemical Society*, (2006), Vol. 128, S1-S8 discloses synthetic procedures for 7-[(trifluoromethoxyphenylazo)phenoxy]pentanoic acid that, when combined with the present disclosure, can be modified to obtain the compounds of formula (I).

FIG. 1B shows one example of a graphene composite that includes an azobenzene compound. Azobenzene compound 120 in photoswitchable layer 110 may be coupled to substrate 105 so that the hydrophobic group, trifluoromethyl, extends towards graphene layer 115 when azobenzene compound 120 is in the trans configuration. When an appropriate radiation is applied to azobenzene compound 120, the compound isomerizes to the cis configuration so that the hydrophobic group faces away from (not shown) graphene layer 115. By modulating the location of the hydrophobic group, the surface properties of photoswitchable layer 110 can be modulated.

The azobenzene compound of formula (I) may, for example, form a self-assembled monolayer on the surface of a substrate. As a specific example, the coupling group on the compound of formula (I) can be a thiol (in uncoupled form) that bonds to a gold substrate to couple the azobenzene compound to the substrate in a monolayer. As another example, the coupling group on the compound of formula (I) can be a silane coupling group, such as trimethoxy silyl or triacetoxysilyl (in uncoupled form), that couples with (e.g., forms a covalent bond with) the surface of a silica substrate. As still another example, the coupling group can be a carboxylic acid (in uncoupled form) on the compound of formula (I) that couples to an amine-containing silane coupling agent, such as 3-aminopropyltrimethoxysilane, which is coupled to the surface of a silica substrate.

In some embodiments, the photoswitchable layer 110 may include a polymer, where the azobenzene compound is conjugated to the polymer. For example, Lee, H. et al., "Phototubable Temperature-Responsive Molecular Brushes Prepared by ATRP," *Macromolecules*, (2006), Vol. 39, pp. 3914-20 discloses 4-methacryloyloxyazobenzene that can be incorporated into various acrylic polymers. As another example, Jiang, W. et al., "Photo-switched wettability on an electrostatic self-assembly azobenzenemonolayer," *Chemical Communications*, (2005), pp. 3550-52 discloses poly {2-[4-phenylazophenoxy] ethyl acrylate-co acrylic acid} (PPAPE) having a ratio of acrylic acid to azobenzene of about 1:1 that can exhibit photoswitchable surface properties. The polymer may have a weight average molecule weight of, for example, at least about 1000 Da, at least about 10,000 Da, or at least about 100,000 Da. In some embodiments, the polymer in the photoswitchable layer may be an electrospun fiber which can provide increased surface area for the photoswitchable layer. In some embodiments, the polymer may be a brush copolymer. For example, amine-containing azobenzene derivatives may be grafted to the side chain of a polymer using various isocyanate-containing crosslinking agents.

In some embodiments, substrate 105 to which photoswitchable layer 110 is applied may have a nanoscale roughness. The nanoscale roughness may provide increased surface area, which may lead to greater number of photoisomerization compounds that can be attached to substrate 105 in forming photoswitchable layer 110, which in turn may provide a larger differential in surface tension of the composite when photoswitchable layer 110 is switched from hydrophilic to hyrdrophobic states, and vice versa (e.g., when the photoisomerization compound is switched between the cis and trans isomers). In some embodiments, the nanoscale roughness includes features having dimensions of about 20 nm or less.

The nanoscale roughness may be obtained, in some embodiments, by providing substrate 105 containing nanoparticles to which the photoisomerization compound can be conjugated in forming photoswitchable layer 110. For example, substrate 105 can contain silica nanoparticles (e.g., a diameter of less than about 50 nm) applied via a negatively charged polymer (e.g., poly(allylamine hydrochloride)) to impart nanoscale roughness. An azobenzene compound may be coupled to the silica nanoparticles using a suitable silane coupling agent or silane coupling group. In some embodiments, the nanoscale roughness may be obtained by applying a comb polymer having azobenzene units grafted to the polymer. In some embodiments, nanoscale roughness may be obtained by applying electrospun polymer fibers (e.g., having a diameter of about 2 nm or less) to the substrate. Azobenzene units may be grafted or coupled to the polymer fibers.

The surface roughness of the substrate can be at least about 0.1 nm, at least about 0.2 nm, at least about 0.5 nm, at least about 1.0 nm, at least about 1.5 nm, at least about 2.0 nm, or at least about 2.5 nm. The surface roughness of the substrate can be up about 1.0 nm, up to about 1.5 nm, up to about 2.0 nm, up to about 2.5 nm, up to about 3.0 nm, up to about 5.0 nm, up to about 7.5 nm, up to about 10.0 nm. The surface roughness can be a range between any two of the aforementioned surface roughness values.

The photoswitchable layer 110 may, for example, have a thickness of greater than or equal to about 1 nm, greater than or equal to about 2 nm, greater than or equal to about 5 nm, or greater than or equal to about 10 nm. The photoswitchable layer 110 may, for example, have a thickness of no more than about 20 nm, no more than about 15 nm, no more than about 10 nm, or no more than about 5 nm. In some embodiments, the photoswitchable layer 110 may have a thickness in the range of about 1 nm to about 20 nm, or in the range of about 2 nm to about 10 nm. The photoswitchable layer 110 may, in some embodiments, be a self-assembled monolayer.

Graphene layer 115 may have varying thicknesses. For example, the thickness may be less than or equal to about 2 nm, less than or equal to about 1.5 nm, less than or equal to about 1.0 nm, less than or equal to about 0.6 nm, or about 0.3 nm. The thickness of the graphene layer may be an amount within a range provided by any two of the aforementioned thickness values. The thickness of the graphene layer may have up to six graphene sheets (e.g., one, two, three, four, five, or six stacked graphene sheets). In some embodiments, the graphene may form a monolayer, such that the thickness is about one-atom thick (e.g., about 0.3 nm thick).

The graphene layer 115 can exhibit a varying water contact angle. Without being bound to any particular theory, it is believed that the thin layer of graphene (e.g., about one-atom thick) can exhibit the surface properties of a layer immediately below the graphene. In other words, the graphene can be "transparent" to van der Waals interactions that affect surface properties. This phenomenon has been described in Rafiee, J. et al., "Wetting transparency of graphene," *Nature Materials*, (2012), pp. 1-6. Thus, the water contact angle of the graphene layer 115 may vary depending on the surface properties of the photoswitchable layer 110, which in turn may be controlled by applying radiation that produces a cis-trans isomerization in the photoswitchable layer 115. In some embodiments the graphene layer 115 may exhibit a water contact angle of at least about 80° when the photoswitchable layer 110 is in the hydrophobic state (e.g., the azobenzene compound of formula (I) is in the trans configuration). In some embodiments, the graphene layer 115 may exhibit a water contact angle of at least about 90° when the photoswitchable layer 110 is in the hydrophobic state. In some embodiments, the graphene layer 115 may exhibit a water contact angle of at least about 100° when the photoswitchable layer 110 is in the hydrophobic state. In some embodiments, the graphene layer 115 may exhibit a water contact angle of at least about 100° when the photoswitchable layer 110 is in the hydrophobic state. In some embodiments, the graphene layer 115 may exhibit a water contact angle of at least about 110° when the photoswitchable layer 110 is in the hydrophobic state. In some embodiments, the graphene layer 115 may exhibit a water contact angle of at least about 120° when the photoswitchable layer 110 is in the hydrophobic state. In some embodiments, the graphene layer 115 may exhibit a water contact angle within a range of any two aforementioned water contact angles when the photoswitchable layer 110 is in the hydrophobic state.

In some embodiments, the graphene layer 115 may exhibit a water contact angle of less than or equal to about 60° when the photoswitchable layer 110 is in the hydrophilic state (e.g., the azobenzene compound of formula (I) is in the cis configuration). In some embodiments, the graphene layer 115 may exhibit a water contact angle of less than or equal to about 50° when the photoswitchable layer 110 is in the hydrophilic state. In some embodiments, the graphene layer 115 may exhibit a water contact angle of less than or equal to about 40° when the photoswitchable layer 110 is in the hydrophilic state. In some embodiments, the graphene layer 115 may exhibit a water contact angle of less than or equal to about 30° when the photoswitchable layer 110 is in the hydrophilic state. In some embodiments, the graphene layer 115 may exhibit a water contact angle of less than or equal to about 20° when the photoswitchable layer 110 is in the hydrophilic state. In some embodiments, the graphene layer 115 may exhibit a water contact angle of less than or equal to about 10° when the photoswitchable layer 110 is in the hydrophilic state. In some embodiments, the graphene layer 115 may exhibit a water contact angle within a range of any two aforementioned water contact angles when the photoswitchable layer 110 is in the hydrophilic state.

In some embodiments, the graphene layer 115 may exhibit a change in the water contact angle when the photoswitchable layer 110 switches from the hydrophilic state (e.g., the azobenzene compound of formula (I) is in the cis configuration) to the hydrophobic state (e.g., the azobenzene compound of formula (I) is in the trans configuration). For example graphene layer 115 may exhibit a first water contact angle when the photoswitchable layer is in the hydrophobic state, and the graphene layer may exhibit a second water contact angle when the photoswitchable layer is in the hydrophilic state, and wherein the difference between the first water contact angle and the second water contact angle is within the range of 5° to 150°. In some embodiments, the difference between the first water contact angle and the second water contact angle is at least about 5°, at least about 10°, at least about 15°, at least about 20°, at least about 25°, at least about 30°, at least about 35°, at least about 40°, at least about 45°, at least about 50°, at least about 55°, at least about 60°, at least about 65°, at least about 70°, at least about 75°, at least about 80°, at least about 85°, at least about 90°, at least about 95°, at least about 100°, at least about 105°, at least about 110°, at least about 115°, at least about 120°, at least about 125°, at least about 130°, at least about 135°, at least about 140°, at least about 145°, or a range between any of the two aforementioned differences between the first water contact angle and the second water contact angle.

Figure 2:
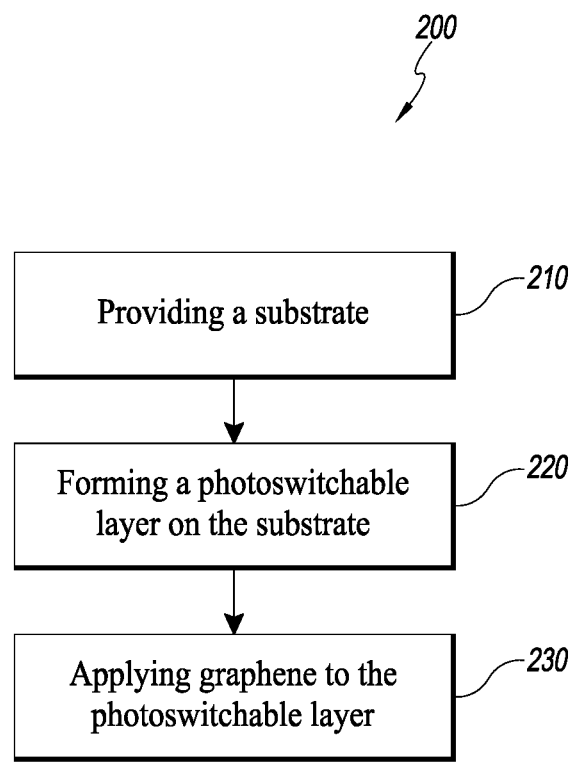
FIG. 2 is a flow diagram illustrating one example of a method of making a graphene composite in accordance with at least some embodiments of the present disclosure.

Some embodiments disclosed herein include a method of making a graphene composite. The method may be used, in some embodiments, to prepare any of the graphene composites disclosed in the present application (e.g., graphene composite 100 as depicted in FIG. 1). FIG. 2 is a flow diagram illustrating one example of a method of making a graphene composite in accordance with at least some embodiments of the present disclosure. As illustrated in FIG. 2, method 200 may include one or more functions, operations, or actions as illustrated by one or more of blocks 210-230.

Processing for method 200 may begin at block 210, "Providing a substrate." Block 210 may be followed by block 220, "Forming a photoswitchable layer on the substrate." Block 220 may be followed by block 230, "Applying graphene to the photoswitchable layer."

In FIG. 2, blocks 210-230, are illustrated as being performed sequentially with the operation(s) at block 210 performed first and the operation(s) at block 230 performed last. These operations may be reordered, combined, and/or divided into additional or different operations as appropriate to suit particular embodiments. In some embodiments, additional operations may be added. In some embodiments, one or more of the operations can be performed at about the same time.

At block 210, "Providing a substrate" can include providing a suitable substrate for forming a photoswitchable layer thereon. The substrate can be, for example, a metal (e.g., gold), a ceramic (e.g., silica), or a polymer (e.g., a polyolefin, acrylic, polyester, and the like). The substrate may be selected based on the chemistry for forming the photoswitchable layer. For example, for self-assembled monolayers including a silane coupling group, the substrate may include a material with hydroxyl groups capable of reacting with the silane coupling group (e.g., silica). As another example, for self-assembled monolayers including a thiol group, the substrate may include a noble metal (e.g., gold) that react with the thiol.

In some embodiments, the substrate can include silica nanoparticles and a negatively charged polymer applied to the substrate with a negatively charged polymer. In some embodiments, the negatively charged polymer may be poly (allylamine hydrochloride). The mixture of nanoparticles and polymer may provide a nanoscale roughness for the photoswitchable layer.

At block 220, "Forming a photoswitchable layer on the substrate," the photoswitchable layer may be formed so as to be configured to reversibly change between a hydrophobic state and a hydrophilic state. The operation(s) at block 220 may, for example, comprise applying a polymer on the substrate. Various techniques may be used for forming the photoswitchable layer depending on the particular photoswitchable compound.

In some embodiments, an azobenzene compound can be conjugated to a polymer and applied to the substrate dispersed in a solvent. The solvent can be removed (e.g., by heating or vacuum) to produce the photoswitchable layer. In some embodiments, the polymer may be formed into electrospun nanofibers that are dispersed in solvent before applying to the substrate. In some embodiments, the azobenzene compound may include a coupling group (e.g., a silane coupling group or thiol) that can be reacted with the substrate using chemisorption techniques.

In some embodiments, an azobenzene compound can be coupled to the substrate, wherein the azobenzene compound comprises a silane coupling agent. In some embodiments, an amine-containing silane coupling agent (e.g., 3-aminopropyltrimethoxysilane) can be coupled to the surface of the substrate, and then an azobenzene compound with a carboxylic acid can be reacted with the amine-containing silane coupling agent.

At block 230, "Applying graphene to the photoswitchable layer" may include applying a mixture to the photoswitchable layer. The mixture may, in some embodiments, include graphene dispersed in a solvent. The mixture may be applied, for example, by dip coating, spin coating, roll coating, spray coating, air knife coating, slot die coating, rod bar coating, or other technique. In some embodiments, graphene can be transferred to the photoswitchable layer using dry transfer with a thermal release tape. See Gaskill, D. et al., "Technique for the Dry Transfer of Epitaxial Graphene onto Arbitrary Substrate," *American Chemical Society Nano*, (2010), Vol. 4(2), pp. 1108-1114. In some embodiments, graphene disposed on polymethylmethacrylate (PMMA) films can be placed on the photoswitchable layer and the PMMA removed using an appropriate solvent. See Ruoff, R. et al., "Transfer of Large-Area Graphene Films for high-Performance Transparent Conductive Electrodes," *Nano Letters*, (2009), Vol. 9(12), pp. 4359-4363.

Figure 3:
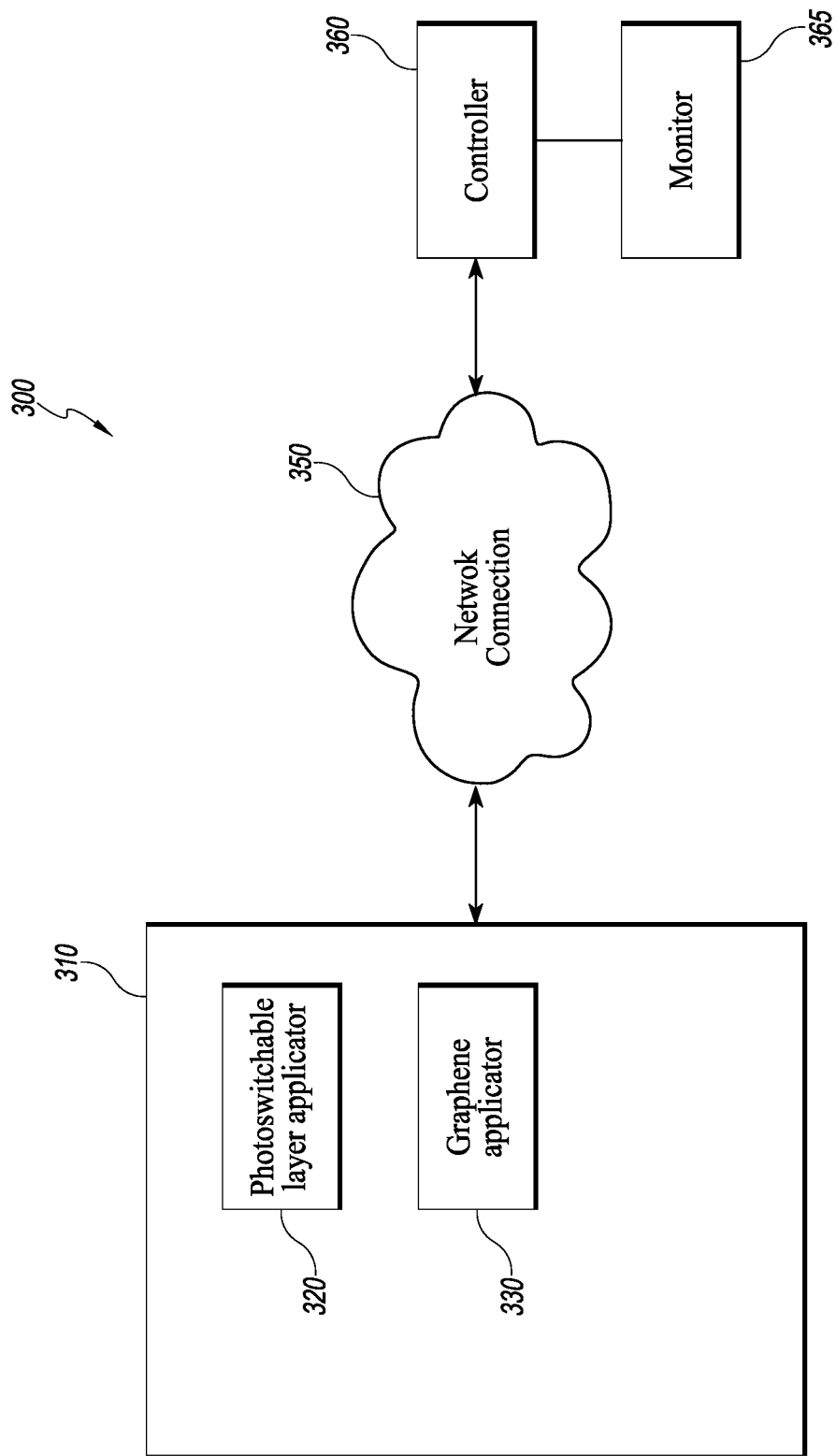
FIG. 3 is a block diagram illustrating one example of a system that is configured to control one or more operations in accordance with at least some embodiments of the present disclosure.

Some embodiments disclosed herein include a system for making a graphene composite. The system may be used, for example, to perform any of the methods disclosed in the present application for making a graphene composite (e.g., method 200 as depicted in FIG. 2). FIG. 3 is a block diagram illustrating one example of a system 300 that may be configured to control one or more operations in accordance with at least some embodiments of the present disclosure. For example, equipment for performing operations for the flow diagram of FIG. 2 may be included in system 300.

System 300 may include a processing plant or facility 310 that is arranged in communication with a controller or processor 360. Processor or controller 360 may be the same or different controller as processor 410 described later with respect to FIGS. 4A-B. In some embodiments, processing plant or facility 310 may be adapted to communicate with controller 360 via a network connection 350. Network connection 350 may be a wireless connection or a wired connection or some combination thereof.

In some embodiments, controller 360 may be adapted to communicate operating instructions for various systems or devices in processing plant or facility 310, which may include, for example, control of one or more operating conditions. Controller 360 may be configured to monitor or receive information from processing plant or facility 310 and utilize the information as feedback to adjust one or more operating instructions communicated to processing plant or facility 310.

In some embodiments, the operating conditions may be presented on a monitor or display 365 and a user may interact with a user interface (not shown) to adapt or adjust various aspects of the processing. Non-limiting examples of aspects of the process that may be presented on monitor or display 365 may include time, temperature, pressure, concentration of graphene oxide, type of photoswitchable compound, and the like. Monitor or display 365 may be in the form of a cathode ray tube, a flat panel screen such as an LED display or LCD display, or any other display device. The user interface may include a keyboard, mouse, joystick, write pen, touch screen, or other device such as a microphone, video camera or other user input device.

In some embodiments, processing plant or facility 310 may include one or more of photoswitchable layer applicator 320 and graphene applicator 330. In some embodiments, photoswitchable layer applicator 320 may be configured via controller 360 to form a photoswitchable layer, or a precursor thereof, to a substrate (e.g., as in operation 220 depicted in FIG. 2). Photoswitchable layer applicator 320 may include one or more of a dip coater, a spin coater, a roll coater, a rod-bar coater, a spray coater, an air knife coater, or a slow-die coater. Controller 360 may be configured to adjust photoswitchable layer applicator 320 to maintain conditions effective to form a photoswitchable layer on the substrate. In some embodiments, photoswitchable layer applicator 320 may be fluidly coupled to one or more reservoirs containing one or more azobenzene compounds. Controller 360 may be configured to adjust valves to control an amount and/or rate of polymer delivered from the one or more reservoirs into photoswitchable layer applicator 320.

Graphene applicator 330 may be configured via controller 360 to apply graphene to the photoswitchable layer (e.g., as in operation 230 depicted in FIG. 2). Graphene applicator 330 may include one or more of dip coater, a spin coater, a roll coater, a rod-bar coater, a spray coater, an air knife coater, a slot-die coater, or other device. Controller 360 may be configured to adjust graphene applicator 330 to maintain conditions effective to apply graphene to the photoswitchable layer, and in some embodiments, such that the graphene layer may have a thickness of about 2 nm or less formed on the photoswitchable layer. In some embodiments, graphene applicator 330 may be fluidly coupled to a reservoir containing graphene dispersed in a solvent. Controller 360 may be configured to adjust a valve to control an amount and/or rate of materials delivered from the reservoir into graphene applicator 330. In some embodiments, graphene applicator 330 can be fluidly coupled to the photoswitchable layer applicator 320 via a valve. Controller 360 may be configured to adjust the valve to control an amount and/or rate of photoswitchable layer delivered from photoswitchable layer applicator 320 into graphene applicator 330.

Figure 4A:
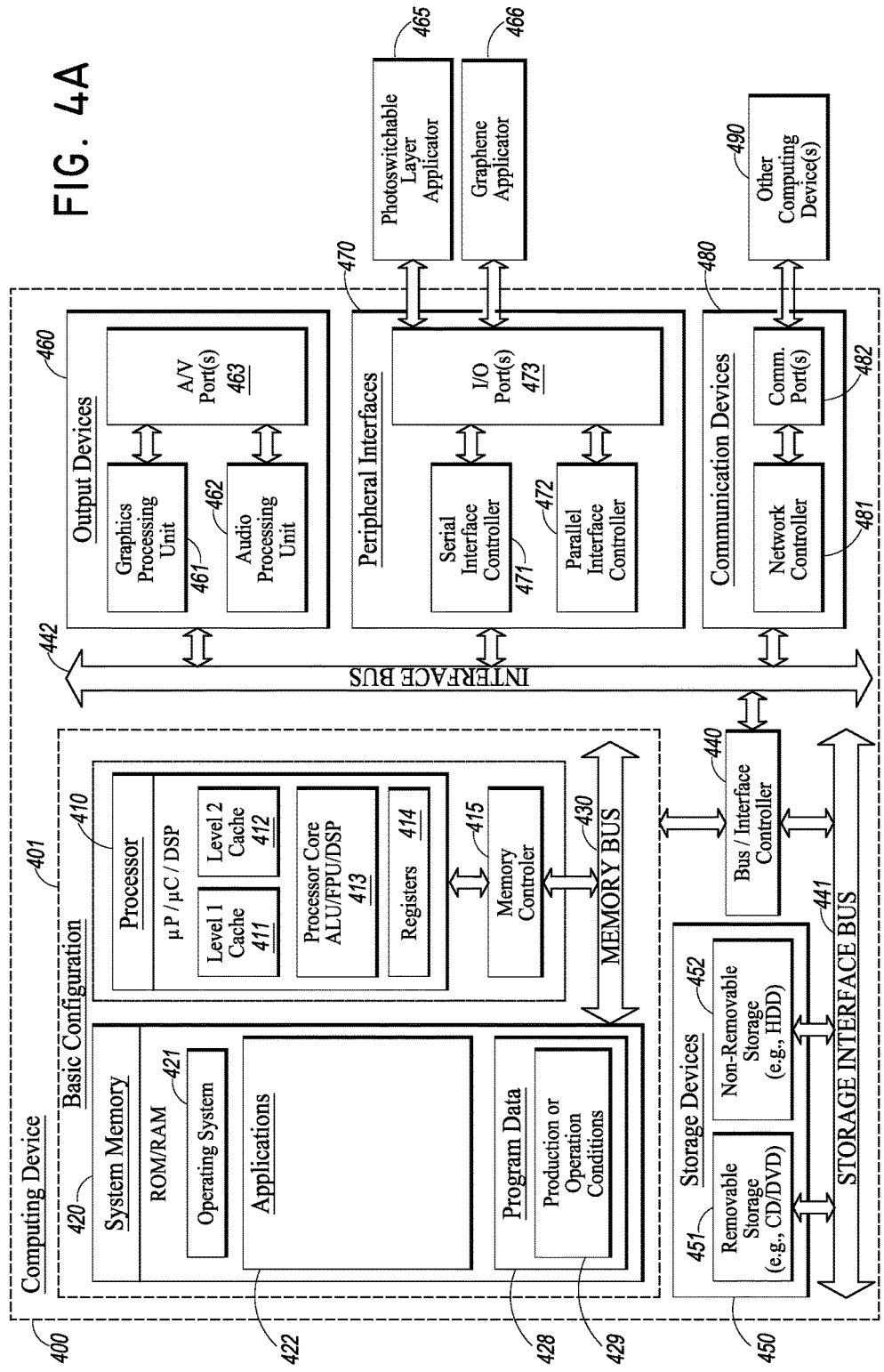
FIGS. 4A-B are block diagrams illustrating one example of a computing device that may be configured to control one or more operations in accordance with at least some embodiments of the present disclosure.
Figure 4B:
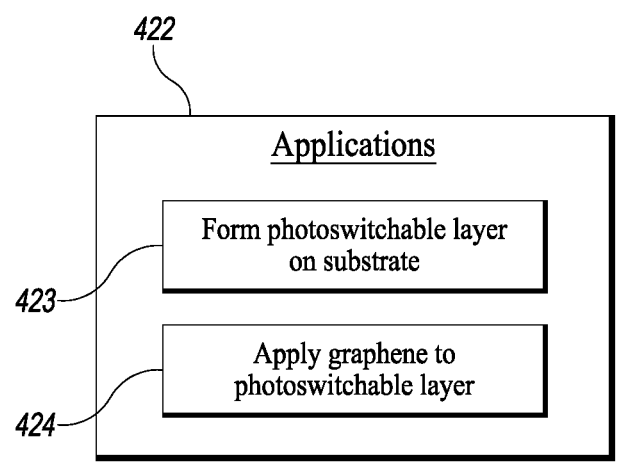

FIGS. 4A-B are block diagrams illustrating one example of a computing device 400 that may be configured to control one or more operations in accordance with at least some embodiments of the present disclosure. For example, operations for the flow diagram of FIG. 2 may be performed and/or controlled by computing device 400. In a very basic configuration, computing device 400 typically includes one or more controllers or processors 410 and system memory 420. A memory bus 430 may be used for communicating between the processor 410 and the system memory 420.

Depending on the desired configuration, processor 410 may be of any type including but not limited to a microprocessor (µP), a microcontroller (µC), a digital signal processor (DSP), or any combination thereof. Processor 410 may include one or more levels of caching, such as a level one cache 411 and a level two cache 412, a processor core 413, and registers 414. The processor core 413 may include an arithmetic logic unit (ALU), a floating point unit (FPU), a digital signal processing core (DSP Core), or any combination thereof. A memory controller 415 may also be used with the processor 410, or in some implementations the memory controller 415 may be an internal part of the processor 410.

Depending on the desired configuration, the system memory 420 may be of any type including but not limited to volatile memory (such as RAM), non-volatile memory (such as ROM, flash memory, etc.), or any combination thereof. System memory 420 typically includes an operating system 421, one or more applications 422, and program data 428. As shown in FIG. 4B, applications 422 may include, for example, computer-executable instructions to "Form photoswitchable layer on substrate" in an application 423 and computer-executable instructions to "Apply to graphene to photoswitchable layer" in an application 424. These applications/instructions may correspond to operation 220 and operation 230, respectively, as depicted in FIG. 2. Returning to FIG. 4A, program data 428 may include, for example, production data and/or operating conditions data 429 that may be used by one or more of applications 423 and 424.

Computing device 400 may have additional features or functionality, and additional interfaces to facilitate communications between the basic configuration 401 and any required devices and interfaces. For example, a bus/interface controller 440 may be used to facilitate communications between the basic configuration 401 and one or more data storage devices 450 via a storage interface bus 441. The data storage devices 450 may be removable storage devices 451, non-removable storage devices 452, or a combination thereof. Examples of removable storage and non-removable storage devices include magnetic disk devices such as flexible disk drives and hard-disk drives (HDDs), optical disk drives such as compact disk (CD) drives or digital versatile disk (DVD) drives, solid state drives (SSDs), and tape drives, to name a few. Example computer storage media may include volatile and nonvolatile, removable and non-removable media implemented in any method or technology for storage of information, such as computer readable instructions, data structures, program modules, or other data.

System memory 420, removable storage 451, and non-removable storage 452 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium that may be used to store the desired information and that may be accessed by computing device 400. Any such computer storage media may be part of device 400.

Computing device 400 may also include an interface bus 442 for facilitating communication from various interface devices (e.g., output interfaces, peripheral interfaces, and communication interfaces) to the basic configuration 401 via the bus/interface controller 440. Example output devices 460 include a graphics processing unit 461 and an audio processing unit 462, which may be configured to communicate to various external devices such as a display or speakers via one or more A/V ports 463. Example peripheral interfaces 470 include a serial interface controller 471 or a parallel interface controller 472, which may be configured to communicate with external devices such as input devices (e.g., keyboard, mouse, pen, voice input device, touch input device, etc.) or other peripheral devices (e.g., printer, scanner, etc.) via one or more I/O ports 473. For example, in some embodiments, a photoswitchable layer applicator 465 and a graphene applicator 466 (which may be similar or the same as photoswitchable layer applicator 320 and graphene applicator 330, respectively, depicted in FIG. 3) may be optionally connected via an I/O port and used to deposit nanostructures onto a substrate. An example communications device 480 includes a network controller 481, which may be arranged to facilitate communications with one or more other computing devices 490 over a network communication via one or more communication ports 482.

The communications connection is one example of a communication media. Communication media may typically be embodied by computer readable instructions, data structures, program modules, or other data in a modulated data signal, such as a carrier wave or other transport mechanism, and include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), infrared (IR), and other wireless media.

Figure 5:
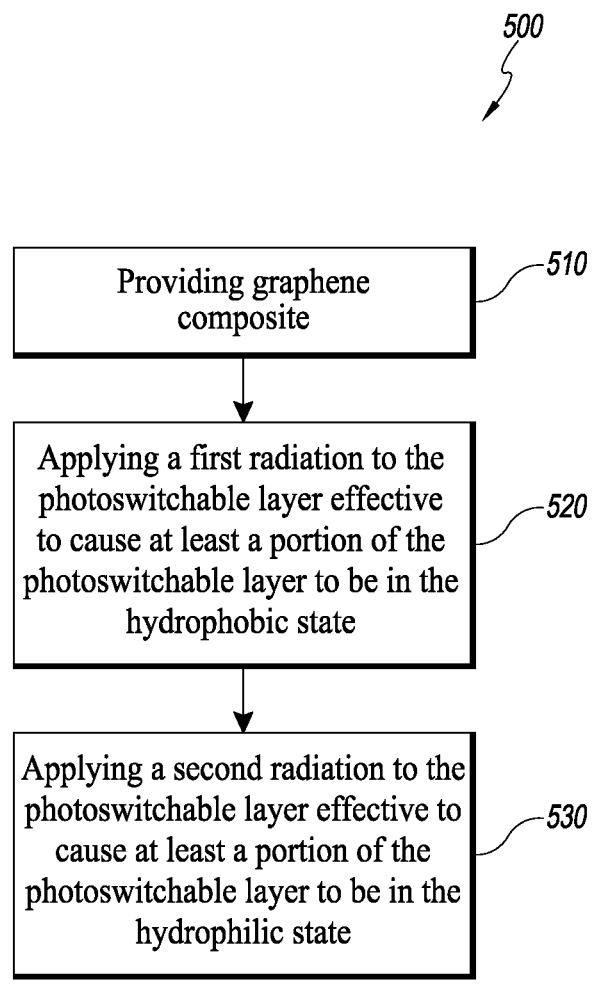
FIG. 5 is a flow diagram illustrating one example of a method of using a graphene composite in accordance with at least some embodiments of the present disclosure.

Some embodiments disclosed herein include a method of using a graphene composite. FIG. 5 is a flow diagram illustrating one example of a method of making a graphene composite in accordance with at least some embodiments of the present disclosure. As illustrated in FIG. 5, method 500 may include one or more functions, operations, or actions as illustrated by one or more of blocks 510-530.

Processing for method 500 may begin at block 510, "Providing a graphene composite." Block 510 may be followed by block 520, "Applying a first radiation to the photoswitchable layer effective to cause at least a portion of the photoswitchable layer to be in the hydrophobic state." In some embodiments, the entire photoswitchable layer is in the hydrophobic state after block 520. Block 520 may be followed by block 530, "Applying a second radiation to the photoswitchable layer effective to cause at least a portion of the photoswitchable layer to be the hydrophilic state." In some embodiments, the entire photoswitchable layer is in the hydrophilic state after block 530.

In FIG. 5, blocks 510-530, are illustrated as being performed sequentially with the operation(s) at block 510 performed first and the operation(s) at block 530 performed last. These operations may be reordered, combined, and/or divided into additional or different operations as appropriate to suit particular embodiments. In some embodiments, additional operations may be added. In some embodiments, one or more of the operations can be performed at about the same time. In some embodiments, block 520 can be performed after block 530.

At block 510, "Providing a graphene composite," a graphene composite may be provided having a photoswitchable layer that may be configured to reversibly change between a hydrophobic state and a hydrophilic state. The photoswitchable layer may be disposed between a substrate and a graphene layer, where the graphene layer is disposed directly on the photoswitchable layer. The graphene composite may, for example, be any of the graphene composites disclosed in the present application (e.g., graphene composite 100 as depicted in FIG. 1). In some embodiments, the photoswitchable layer may have a nanoscale roughness. In some embodiments, the photoswitchable layer may include at least one azobenzene compound (e.g., the azobenzene compound of formula (I)). The graphene layer may, in some embodiments, have a thickness less than or equal to about 2 nm. In some embodiments, the graphene layer may include no more than six graphene sheets along its thickness.

At block 520, "Applying a first radiation to the photoswitchable layer effective to cause at least a portion of the photoswitchable layer to be in the hydrophobic state," the first radiation may be applied so that the graphene layer exhibits a hydrophobic state. In some embodiments, the first radiation can be a visible light (e.g., a wavelength of peak emission about 400 nm to about 700 nm). As discussed above, the first radiation may result in a trans configuration for an azobenzene compound that results in hydrophobic surface properties for the photoswitchable layer. The graphene layer disposed on the photoswitchable layer may therefore also exhibit hydrophobic properties.

In some embodiments, the first radiation can be applied to the photoswitchable layer such that the graphene layer has a water contact angle of at least about 80°. In some embodiments, the first radiation can be applied to the photoswitchable layer such that the graphene layer has a water contact angle of at least about 90°. In some embodiments, the first radiation can be applied to the photoswitchable layer such that the graphene layer has a water contact angle of at least about 100°. In some embodiments, the first radiation can be applied to the photoswitchable layer such that the graphene layer has a water contact angle of at least about 110°.

In some embodiments, applying the first radiation results in a change in the water contact angle of the graphene layer. For example, applying the first radiation may result in a change in the water contact angle of the graphene layer of 5° to 150°. In some embodiments, the change in the water contact angle is at least about 5°, at least about 10°, at least about 15°, at least about 20°, at least about 25°, at least about 30°, at least about 35°, at least about 40°, at least about 45°, at least about 50°, at least about 55°, at least about 60°, at least about 65°, at least about 70°, at least about 75°, at least about 80°, at least about 85°, at least about 90°, at least about 95°, at least about 100°, at least about 105°, at least about 110°, at least about 115°, at least about 120°, at least about 125°, at least about 130°, at least about 135°, at least about 140°, at least about 145°, or a range between any of the two aforementioned values.

At block 530, "Applying a second radiation to the photoswitchable layer effective to cause at least a portion of the photoswitchable layer to be in the hydrophilic state," the second radiation may be applied so that the graphene layer exhibits a hydrophilic state. In some embodiments, the second radiation can be an ultraviolet light (e.g., a wavelength of peak emission of about 400 nm to or less). In some embodiments, the first radiation has a wavelength of peak emission that is greater than a wavelength of peak emission for the second radiation. For example, the wavelength of peak emission for the first radiation is at least about 50 nm greater than the wavelength of peak emission for the second radiation. As discussed above, the second radiation may result in a cis configuration for an azobenzene compound that results in hydrophilic surface properties for the photoswitchable layer. The graphene layer disposed on the photoswitchable layer may therefore also exhibit hydrophilic properties.

In some embodiments, the second radiation can be applied to the photoswitchable layer such that the graphene layer has a water contact angle of no more than about 60°. In some embodiments, the second radiation can be applied to the photoswitchable layer such that the graphene layer has a water contact angle of no more than about 50°. In some embodiments, the second radiation can be applied to the photoswitchable layer such that the graphene layer has a water contact angle of no more than about 40°. In some embodiments, the second radiation can be applied to the photoswitchable layer such that the graphene layer has a water contact angle of no more than about 30°. In some embodiments, the second radiation can be applied to the photoswitchable layer such that the graphene layer has a water contact angle of no more than about 20°.

In some embodiments, applying the second radiation results in a change in the water contact angle of the graphene layer. For example, applying the second radiation may result in a change in the water contact angle of the graphene layer of 5° to 150°. In some embodiments, the change in the water contact angle is at least about 5°, at least about 10°, at least about 15°, at least about 20°, at least about 25°, at least about 30°, at least about 35°, at least about 40°, at least about 45°, at least about 50°, at least about 55°, at least about 60°, at least about 65°, at least about 70°, at least about 75°, at least about 80°, at least about 85°, at least about 90°, at least about 95°, at least about 100°, at least about 105°, at least about 110°, at least about 115°, at least about 120°, at least about 125°, at least about 130°, at least about 135°, at least about 140°, at least about 145°, or a range between any of the two aforementioned values.

Figure 6:
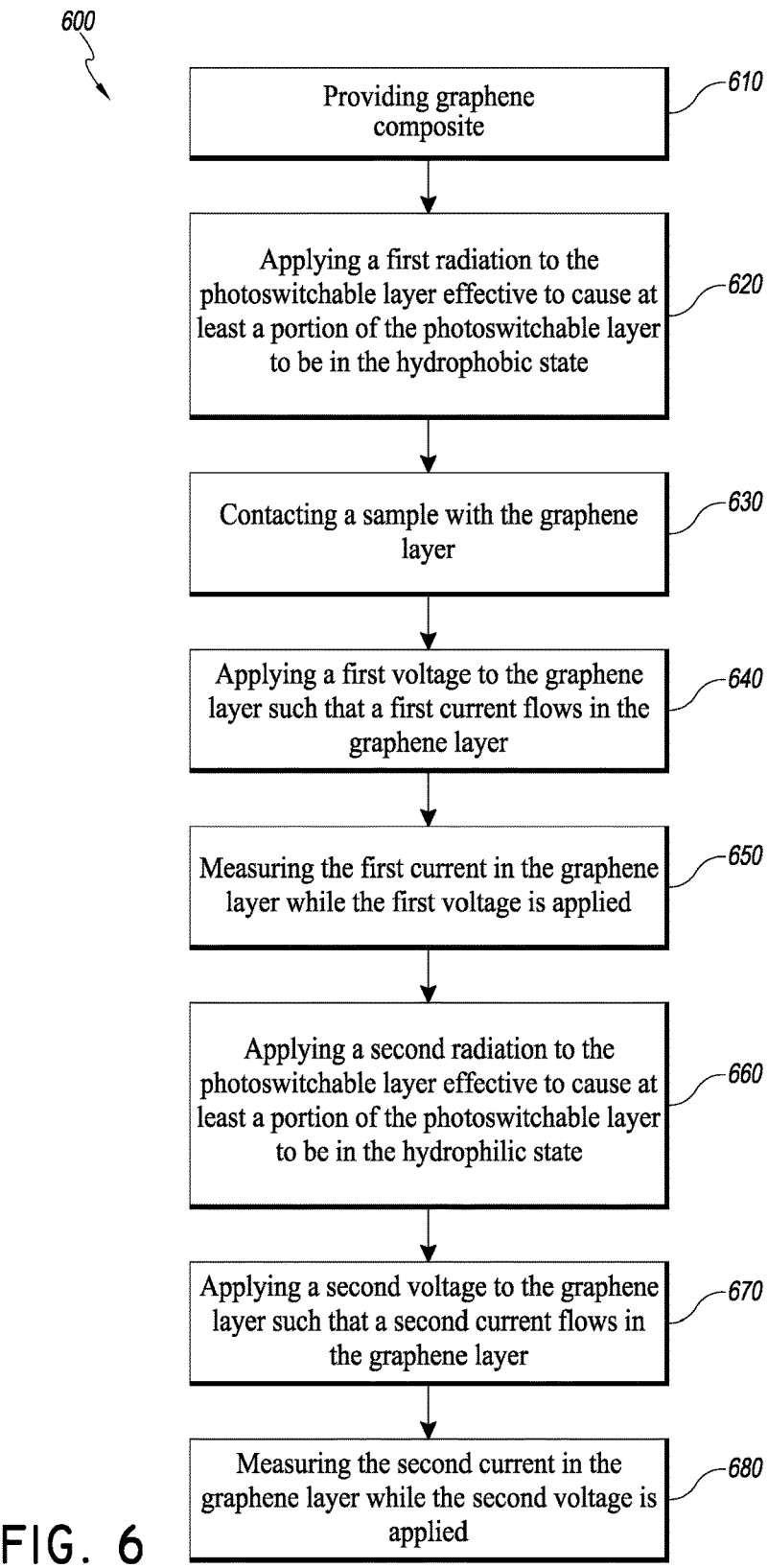
FIG. 6 is a flow diagram illustrating one example of a method of sensing one or more analytes in a sample in accordance with at least some embodiments of the present disclosure.
Figure 7:
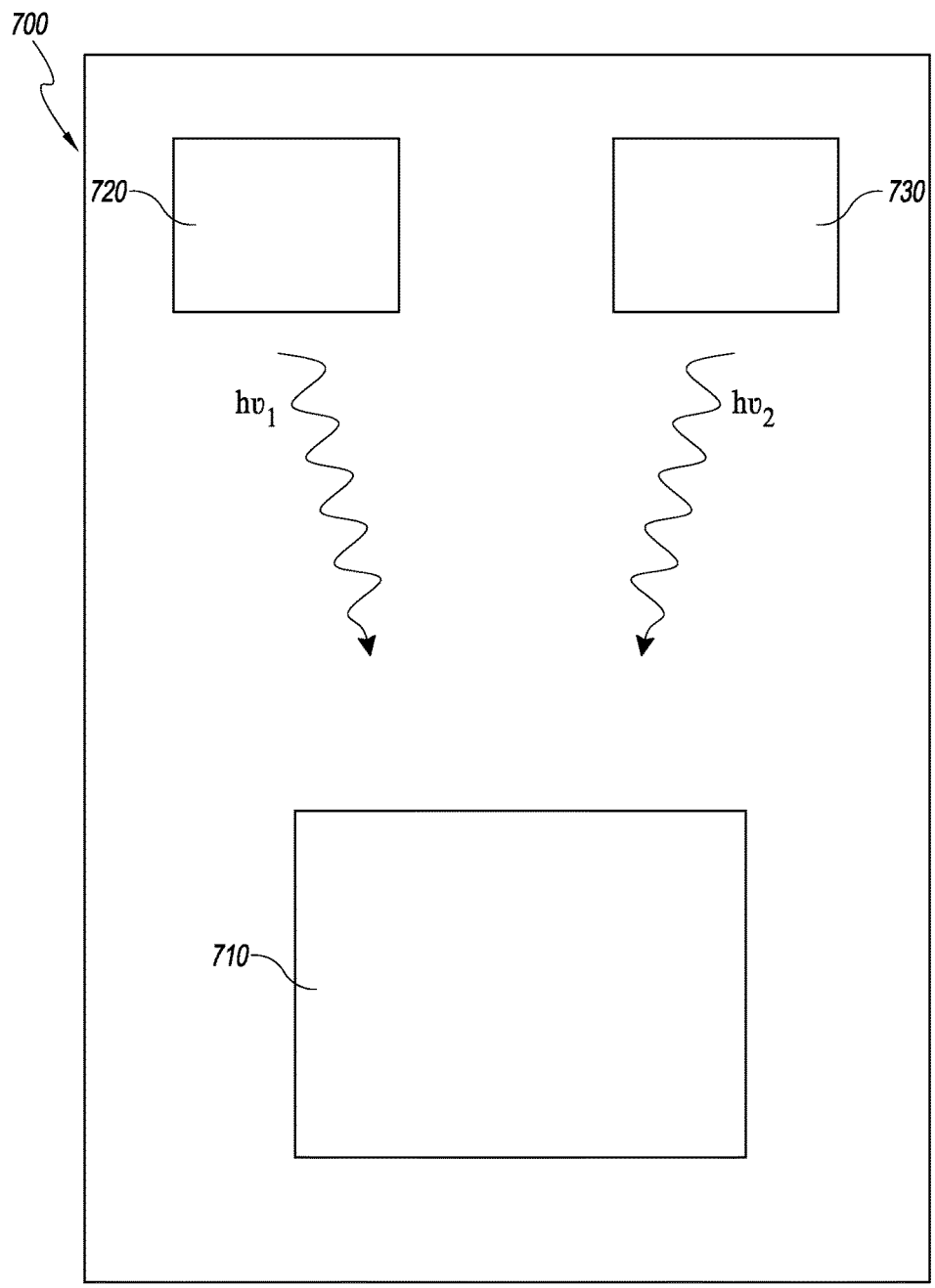
FIG. 7 is a block diagram illustrating one example of a device that may be configured to use a graphene composite in accordance with at least some embodiments of the present disclosure.

Some embodiments disclosed herein include a method of sensing one or more analytes in a sample. FIG. 6 is a flow diagram illustrating one example of a method of sensing one or more analytes in a sample in accordance with at least some embodiments of the present disclosure. As illustrated in FIG. 6, method 600 may include one or more functions, operations, or actions as illustrated by one or more of blocks 610-680.

Processing for method 600 may begin at block 610, "Providing a graphene composite." Block 610 may be followed by block 620, "Applying a first radiation to the photoswitchable layer effective to cause at least a portion of the photoswitchable layer to be in the hydrophobic state." In some embodiments, the entire photoswitchable layer is in the hydrophobic state after block 620. Block 620 may be followed by block 630, "Contacting a sample with the graphene layer." Block 630 may be followed by block 640, "Applying a first voltage to the graphene layer such that a first current flows in the graphene layer." Block 640 may be followed by block 650, "Measuring the first current in the graphene layer while the first voltage is applied." Block 650 may be followed by block 660, "Applying a second radiation to the photoswitchable layer effective to cause at least a portion of the photoswitchable layer to be in the hydrophilic state." In some embodiments, the entire photoswitchable layer is in the hydrophilic state after block 660. Block 660 may be followed by block 670, "Applying a second voltage to the graphene layer such that a second current flows in the graphene layer." Block 670 may be followed by Block 680, "Measuring the second current in the graphene layer while the second voltage is applied."

In FIG. 6, blocks 610-680, are illustrated as being performed sequentially with the operation(s) at block 610 performed first and the operation(s) at block 680 performed last. These operations may be reordered, combined, and/or divided into additional or different operations as appropriate to suit particular embodiments. In some embodiments, additional operations may be added. In some embodiments, one or more of the operations can be performed at about the same time.

At block 610, "Providing a graphene composite," the graphene composite may have a photoswitchable layer that may be configured to reversibly change between a hydrophobic state and a hydrophilic state and that may be disposed between a substrate and a graphene layer, where the graphene layer is disposed directly on the photoswitchable layer. The graphene composite may, for example, be any of the graphene composites disclosed in the present application (e.g., graphene composite 100 as depicted in FIG. 1). In some embodiments, the photoswitchable layer may include at least one azobenzene compound.

At block 620, "Applying a first radiation to the photoswitchable layer effective to cause at least a portion of the photoswitchable layer to be in the in the hydrophobic state," radiation can be applied to obtain hydrophobic surface properties for the graphene layer. Generally, block 620 can have the same characteristics as described above with regard to block 520 as depicted in FIG. 5.

At block 630, "Contacting a sample with the graphene layer," a sample is contacted with the graphene layer. The sample can be any fluid (e.g., a gas or liquid) in which one or more analytes may be sensed. The sample may be, for example, a sample of air or water. The method of contacting the sample to the graphene layer is not particularly limited, and may include, for example, exposing the graphene layer to an ambient air or placing the graphene composite in a sealed container with a sample of gas. The sample may be contacted with the graphene layer before, after, or during performing the operation(s) at block 620.

At block 640, "Applying a first voltage to the graphene layer such that a first current flows in the graphene layer," a first voltage can be applied to produce a first current in the graphene layer. The first voltage may be applied, for example, using a voltage source coupled to electrode pads in contact with the graphene layer.

At block 650, "Measuring the first current in the graphene layer while the first voltage is applied," the first current in the graphene layer can be determined. For example, an ammeter can be coupled to the graphene layer to determine the first current. The measured first current may be optionally correlated with an amount of one or more analytes in the sample. For example, the measured first current may increase with an amount of analyte, and therefore a look-up table or empirical equation (e.g., a linear regression, such as a polynomial fit) can be used to determine an amount of an analyte. The methods provided herein can be applied to an analyte for which a wettability sensor would be effective. Non-limiting example of analytes that may be correlated with the current include aromatic, nucleotides, pesticides, polyaromatic hydrocarbons (PAHs), and metal ions. Also use as a sensor for distinguishing between enantiomers, such as sensors with chrial molecules such as L-dipeptide units.

At block 660, "Applying a second radiation to the photoswitchable layer effective to cause at least a portion of the photoswitchable layer to be in the in the hydrophilic state," radiation can be applied to obtain hydrophilic surface properties for the graphene layer. Generally, block 660 can have the same characteristics as described above with regard to block 530 as depicted in FIG. 5. In some embodiments, block 660 may be performed before block 620.

At block 670, "Applying a second voltage to the graphene layer such that a second current flows in the graphene layer," a second voltage can be applied to produce a second current in the graphene layer. The second voltage may be applied, for example, using a voltage source couple to electrode pads in contact with the graphene layer. The second voltage may be about the same or different that the first voltage applied in block 640.

At block 680, "Measuring the second current in the graphene layer while the second voltage is applied," the second current in the graphene layer can be determined. For example, an ammeter can be coupled to the graphene layer to determine the current. The measured second current may be optionally correlated with an amount of one or more analytes in the sample. For example, the measured second current may increase with an amount of analyte, and therefore a look-up table or empirical equation (e.g., a linear regression) can be used to determine an amount of analyte. In some embodiments, the measurements from block 650 and block 680 may be used together to correlate an amount of a particular analyte. In some embodiments, the measurements from block 650 and block 680 may be separately used in correlations for different analytes.

Some embodiments disclosed herein include a device 700 including a graphene composite 710, a first light source 720 configured to apply a first radiation to the photoswitchable layer effective to cause at least a portion of the photoswitchable layer to be in the hydrophobic state, and a second light source 730 configured to apply a second radiation to the photoswitchable layer effective to cause at least a portion of the photoswitchable layer to be in the hydrophilic state. The graphene composite may, for example, be any of the graphene composites disclosed in the present application (e.g., graphene composite 100 as depicted in FIG. 1). In some embodiments, the graphene composite 710 may include a photoswitchable layer configured to reversibly change between a hydrophobic state and a hydrophilic state, a graphene layer disposed directly on the photoswitchable layer; and a substrate, where the photoswitchable layer may be disposed between the substrate and the graphene layer.

The first light source 720 may, for example, be configured to apply the first radiation to the photoswitchable layer such that the graphene layer has a water contact angle of at least about 80°. In some embodiments, the first light source 720 may, be configured to apply the first radiation to the photoswitchable layer such that the graphene layer has a water contact angle of at least about 90°. In some embodiments, the first light source 720 may, be configured to apply the first radiation to the photoswitchable layer such that the graphene layer has a water contact angle of at least about 100°. In some embodiments, the first light source 720 may, be configured to apply the first radiation to the photoswitchable layer such that the graphene layer has a water contact angle of at least about 110°. The first light source 720 may be configured to emit visible light (e.g., a wavelength of peak emission in the range of about 400 nm to about 700 nm).

In some embodiments, applying radiation from first light source 720 results in a change in the water contact angle of the graphene layer. For example, applying radiation from first light source 720 may result in a change in the water contact angle of the graphene layer of 5° to 150°. In some embodiments, the change in the water contact angle is at least about 5°, at least about 10°, at least about 15°, at least about 20°, at least about 25°, at least about 30°, at least about 35°, at least about 40°, at least about 45°, at least about 50°, at least about 55°, at least about 60°, at least about 65°, at least about 70°, at least about 75°, at least about 80°, at least about 85°, at least about 90°, at least about 95°, at least about 100°, at least about 105°, at least about 110°, at least about 115°, at least about 120°, at least about 125°, at least about 130°, at least about 135°, at least about 140°, at least about 145°, or a range between any of the two aforementioned values.

The second light source 730 may, for example, be configured to apply the second radiation to the photoswitchable layer such that the graphene layer has a water contact angle of less than or equal to about 60°. In some embodiments, the second light source 730 may be configured to apply the second radiation to the photoswitchable layer such that the graphene layer has a water contact angle of less than or equal to about 50°. In some embodiments, the second light source 730 may be configured to apply the second radiation to the photoswitchable layer such that the graphene layer has a water contact angle of less than or equal to about 40°. In some embodiments, the second light source 730 may be configured to apply the second radiation to the photoswitchable layer such that the graphene layer has a water contact angle of less than or equal to about 30°. In some embodiments, the second light source 730 may be configured to apply the second radiation to the photoswitchable layer such that the graphene layer has a water contact angle of less than or equal to about 20°. The second light source 730 may be configured to emit ultraviolet light (e.g., a wavelength of peak emission in the range of about 400 or less). The second light source 730 may also be configured to emit radiation having a wavelength of peak emission that is less than a wavelength of peak emission for the first light source.

In some embodiments, applying radiation from second light source 730 results in a change in the water contact angle of the graphene layer. For example, applying radiation from second light source 730 may result in a change in the water contact angle of the graphene layer of 5° to 150°. In some embodiments, the change in the water contact angle is at least about 5°, at least about 10°, at least about 15°, at least about 20°, at least about 25°, at least about 30°, at least about 35°, at least about 40°, at least about 45°, at least about 50°, at least about 55°, at least about 60°, at least about 65°, at least about 70°, at least about 75°, at least about 80°, at least about 85°, at least about 90°, at least about 95°, at least about 100°, at least about 105°, at least about 110°, at least about 115°, at least about 120°, at least about 125°, at least about 130°, at least about 135°, at least about 140°, at least about 145°, or a range between any of the two aforementioned values.

Device 700 may be used as a sensor. Without intending to be limited to the following embodiment, an example follows for use of device 700 as a sensor. Device 700 may be coupled with a flow chamber configured to flow analyte-containing fluid along the surface of graphene composite 710; in such configuration, the surface of graphene composite 710 can act, for example, as a stationary phase in a chromatographic device. Prior to initiation of flowing analyte-containing fluid, the surface of graphene composite 710 can be configured to be hydrophilic or hydrophobic, according to user preference. During the course of flowing analyte-containing fluid or subsequent to the termination of flowing analyte-containing fluid, the surface of graphene composite 710 can be modified using first light source 720 or second light source 730 to partially or completely modify the surface of graphene composite 710 from hydrophobic to hydrophilic, or from hydrophilic to hydrophobic, depending on user preference and the initial condition of the surface of graphene composite 710. In such a process, analyte can be bound or eluted at different times according to the affinity of the analyte to the surface of graphene composite 710 over the course of the chromatographic process.

The graphene layer of the present application can be used in a variety of configurations in a device such as a sensor device. In some embodiments, the graphene layer may be a transparent cover of a device. In some embodiments, the graphene layer may be an impermeable cover of a device, such as a liquid-impermeable cover or a gas-impermeable cover of a device. In some embodiments, the graphene layer may be a transparent, impermeable cover for a device.

With respect to the use of substantially any plural and/or singular terms herein, those having skill in the art can translate from the plural to the singular and/or from the singular to in the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

EXAMPLES

Additional embodiments are disclosed in further detail in the following examples, which are intended to be illustrative and are not in any way intended to limit the scope of the claims.

Example 1—Preparation of a Graphene Layer on a Polymeric Substrate

The following example demonstrates depositing a monolayer of graphene on an optionally textured polymeric substrate.

Large-area monolayer graphene films are synthesized by chemical vapor deposition on Cu foils using the liquid precursor hexane. After growth a thin, poly(methylmethacrylate) film are coated on the graphene/Cu substrate. The underlying Cu substrate is dissolved in dilute $HNO_3$.

The film is then transferred onto various polymeric surfaces/substrates. The method uses a sacrificial 'self-releasing' polymer layer placed between the conventional PDMS stamp and the graphene to be transferred. The self-releasing layer provides a low work of adhesion on the stamp, which facilitates delamination of the graphene and its placement on the new substrate. See method described in: Song, J. et. al., A general method for transferring graphene onto soft surfaces, Nature Nanotechnology, 8, 2013, 356-362.

The azobenzene-treated surface is CF3AZO, 7-[(trifluoromethoxyphenyl-azo)phenoxy]pentanoic acid. See Prescher, D., Thiele, T., Ruhmann, R., Schulz, G., J. Fluorine Chem. 1995, 74, 185.

What is claimed is:

1. A graphene composite, comprising:
   a photoswitchable layer configured to reversibly change between a state wherein the photoswitchable layer exhibits a first level of hydrophobicity and a state wherein the photoswitchable layer exhibits a second level of hydrophobicity different from the first level, the photoswitchable layer including at least one azobenzene compound and an electrospun nanofiber;
   a graphene layer disposed on the photoswitchable layer; and
   a substrate,
   wherein the photoswitchable layer is disposed between the substrate and the graphene layer.

2. The graphene composite of claim 1, wherein the at least one azobenzene compound is represented by a formula:

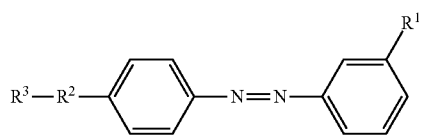

(I)

wherein $R^1$ is a first functional group, $R^2$ is a spacer group, and $R^3$ is a second functional group.

3. The graphene composite of claim 2, wherein the first functional group includes an alkyl, a haloalkyl, an alkoxy, a haloalkoxy, or a halogen.

4. The graphene composite of claim 2, wherein the spacer group includes a $C_{1-20}$-alkylene.

5. The graphene composite of claim 2, wherein the second functional group includes an amine, a carboxylic acid, a thiol, or a silane coupling group.

6. The graphene composite of claim 1, wherein the photoswitchable layer further comprises a polymer, wherein the at least one azobenzene compound is conjugated to the polymer.

7. The graphene composite of claim 6, wherein the polymer includes a brush copolymer.

8. The graphene composite of claim 1, wherein one or more of:
   the photoswitchable layer has a thickness in the range of about 1 nm to about 20 nm;
   the graphene layer has a thickness in the range of about 0.3 nm to about 2 nm; or
   the graphene layer has a thickness of one to six graphene sheets.

9. The graphene composite of claim 1, wherein the graphene layer exhibits one or more of:
   a water contact angle in the range of about 80° to about 120° when the photoswitchable layer is in the state wherein the photoswitchable layer exhibits the first level of hydrophobicity;
   a water contact angle in the range of about 10° to about 60° when the photoswitchable layer is in the state wherein the photoswitchable layer exhibits the second level of hydrophobicity; or
   the graphene layer exhibits a first water contact angle when the photoswitchable layer is in the state wherein the photoswitchable layer exhibits the first level of hydrophobicity, and the graphene layer exhibits a second water contact angle when the photoswitchable layer is in the state wherein the photoswitchable layer exhibits the second level of hydrophobicity, and wherein a difference between the first water contact angle and the second water contact angle is within a range of 5° to 150°.

10. The graphene composite of claim 1, wherein the graphene layer is disposed within 3.0 nm, 2.5 nm, 2.0 nm, or 1.5 nm of the photoswitchable layer; or directly on the photoswitchable layer.

11. The graphene composite of claim 1, wherein the substrate comprises silicon or silica.

12. A method to make a graphene composite, the method comprising:
   providing a substrate;
   forming a photoswitchable layer on the substrate, the photoswitchable layer being configured to reversibly change between a state wherein the photoswitchable layer exhibits a first level of hydrophobicity and a state wherein the photoswitchable layer exhibits a second level of hydrophobicity different from the first level, the photoswitchable layer including at least one azobenzene compound and an electrospun nanofiber; and
   applying graphene to the photoswitchable layer.

13. The method of claim 12, wherein forming the photoswitchable layer on the substrate comprises applying a polymer on the substrate, wherein the polymer comprises the at least one azobenzene compound conjugated to the polymer.

14. The method of claim 12, wherein forming the photoswitchable layer on the substrate comprises:
applying a polymer on the substrate; and
conjugating the at least one azobenzene compound to the polymer.

15. The method of claim 12, wherein forming the photoswitchable layer on the substrate comprises conjugating the at least one azobenzene compound with the substrate, wherein the at least one azobenzene compound comprises a silane coupling agent.

16. The method of claim 12, wherein forming the photoswitchable layer on the substrate comprises:
conjugating an amine-containing silane coupling agent with a surface of the substrate; and
reacting the at least one azobenzene compound with the amine-containing silane coupling agent conjugated to the surface of the substrate.

17. A method, comprising:
providing a graphene composite comprising:
a photoswitchable layer configured to reversibly change between a state wherein the photoswitchable layer exhibits a first level of hydrophobicity and a state wherein the photoswitchable layer exhibits a second level of hydrophobicity different from the first level, the photoswitchable layer including at least one azobenzene compound and an electrospun nanofiber;
a graphene layer disposed on the photoswitchable layer; and
a substrate, wherein the photoswitchable layer is disposed between the substrate and the graphene layer;
applying a first radiation to the photoswitchable layer effective to cause at least a portion of the photoswitchable layer to be in the state wherein the photoswitchable layer exhibits the first level of hydrophobicity; and
applying a second radiation to the photoswitchable layer effective to cause at least a portion of the photoswitchable layer to be in the state wherein the photoswitchable layer exhibits the second level of hydrophobicity.

18. The method of claim 17, wherein the first radiation has a wavelength of peak emission greater than 400 nm and the second radiation has a wavelength of peak emission less than 400 nm.

19. The method of claim 17, wherein at least one of:
applying the first radiation to the photoswitchable layer comprises applying the first radiation to the photoswitchable layer such that the graphene layer has a water contact angle of at least about 80°;
applying the second radiation to the photoswitchable layer comprises applying the second radiation to the photoswitchable layer such that the graphene layer has a water contact angle of less than or equal to about 60°; or
wherein the graphene layer exhibits a first water contact angle when the photoswitchable layer is in the state wherein the photoswitchable layer exhibits a first level of hydrophobicity, and the graphene layer exhibits a second water contact angle when the photoswitchable layer is in the state wherein the photoswitchable layer exhibits a second level of hydrophobicity, and wherein a difference between the first water contact angle and the second water contact angle is within a range of 5° to 150°.

20. The method of claim 17, further comprising:
prior to applying the second radiation to the photoswitchable layer,
contacting a sample having one or more analytes with the graphene layer while the photoswitchable layer is in the state wherein the photoswitchable layer exhibits a first level of hydrophobicity;
applying a first voltage to the graphene layer such that a first current flows in the graphene layer; and
measuring the first current in the graphene layer while the first voltage is applied.

21. The method of claim 20, further comprising:
after applying the second radiation to the photoswitchable layer, applying a second voltage to the graphene layer such that a second current flows in the graphene layer; and
measuring the second current in the graphene layer while the second voltage is applied.

* * * * *